US012778671B2

(12) United States Patent
Takahashi

(10) Patent No.: US 12,778,671 B2
(45) Date of Patent: Nov. 3, 2026

(54) MEDICAL DEVICE

(71) Applicant: TERUMO KABUSHIKI KAISHA, Tokyo (JP)

(72) Inventor: Yusuke Takahashi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 239 days.

(21) Appl. No.: 18/397,110

(22) Filed: Dec. 27, 2023

(65) Prior Publication Data

US 2024/0122644 A1 Apr. 18, 2024

Related U.S. Application Data

(63) Continuation of application No. PCT/JP2022/016473, filed on Mar. 31, 2022.

(30) Foreign Application Priority Data

Jul. 9, 2021 (JP) ................................ 2021-114255

(51) Int. Cl.

*A61B 18/14* (2006.01)
*A61B 17/00* (2006.01)
*A61B 18/00* (2006.01)

(52) U.S. Cl.

CPC *A61B 18/1492* (2013.01); *A61B 2017/00252* (2013.01); *A61B 2018/0016* (2013.01);
(Continued)

(58) Field of Classification Search

CPC ........ A61B 18/1492; A61B 2018/0016; A61B 2018/00267; A61B 2018/0038;
(Continued)

(56) References Cited

U.S. PATENT DOCUMENTS 7,938,826 B2 5/2011 Davis et al.
11,439,460 B2 * 9/2022 Sliwa .................. A61B 5/4836
(Continued)

FOREIGN PATENT DOCUMENTS

WO 2007140420 A2 12/2007
WO 2019085841 A1 5/2019
(Continued)

OTHER PUBLICATIONS

International Search Report (PCT/ISA/210) with translation and Written Opinion (PCT/ISA/237) mailed on Jun. 21, 2022, by the Japan Patent Office as the International Searching Authority for International Application No. PCT/JP2022/016473. (8 pages).

*Primary Examiner* — Beverly M Flanagan

(74) *Attorney, Agent, or Firm* — .Buchanan Ingersoll & Rooney PC

(57) ABSTRACT

A medical device is disposed that is able to prevent short-circuit of a contact portion between an electrode portion and a conductive wire with another contact portion that is electrically independent. A medical device includes an expansion body that is configured to expand and contract in a radial direction, an elongated shaft portion including a proximal end fixing portion to which a proximal end of the expansion body is fixed, a plurality of electrode assemblies including a plurality of electrode portions disposed along the expansion body, and a conductive wire portion disposed in the shaft portion and connected to the electrode assembly with a contact portion, in which at least two or more electrode assemblies are electrically independent, and two or more of the contact portions respectively connected to the two or more electrode assemblies are disposed at different positions in an axial direction in the shaft portion.

16 Claims, 9 Drawing Sheets

(52) U.S. Cl.
CPC ............... *A61B 2018/00267* (2013.01); *A61B 2018/0038* (2013.01); *A61B 2018/00595* (2013.01); *A61B 2018/142* (2013.01)

(58) Field of Classification Search
CPC .... A61B 2018/00595; A61B 2018/142; A61B 2017/00252
USPC ............................................................ 606/41
See application file for complete search history.

(56) References Cited

U.S. PATENT DOCUMENTS

| | | | | |
|---|---|---|---|---|
| 2008/0033421 | A1 | 2/2008 | Davis et al. | |
| 2011/0213364 | A1 | 9/2011 | Davis et al. | |
| 2015/0327923 | A1* | 11/2015 | Just ........................ | A61B 5/287 606/41 |
| 2020/0261704 | A1 | 8/2020 | Wang et al. | |
| 2021/0007791 | A1 | 1/2021 | Takahashi et al. | |
| 2022/0211430 | A1 | 7/2022 | Takahashi | |

FOREIGN PATENT DOCUMENTS

| | | | |
|---|---|---|---|
| WO | 2019189079 | A1 | 10/2019 |
| WO | 2021065874 | A1 | 4/2021 |

* cited by examiner

MEDICAL DEVICE

CROSS-REFERENCES TO RELATED APPLICATIONS

This application is a continuation of International Application No. PCT/JP2022/016473 filed on Mar. 31, 2022, which claims priority to Japanese Patent Application No. 2021-114255 filed on Jul. 9, 2021, the entire content of both of which is incorporated herein by reference.

TECHNOLOGICAL FIELD

The present disclosure generally relates to a medical device that applies energy to a biological tissue.

BACKGROUND DISCUSSION

A medical device is known that includes an electrode portion disposed on an expansion body that expands and contracts in a living body, and performs treatment by ablation for cauterizing a biological tissue by a high-frequency current from the electrode portion. As one of the treatments by ablation, a shunt treatment on the atrial septum is known. The shunt treatment can alleviate heart failure symptoms of a patient with heart failure by forming a shunt (puncture hole) serving as an escape route for an increased atrial pressure in a fossa ovalis of the atrial septum of the patient. In the shunt treatment, the atrial septum is accessed using an intravenous approaching method, and a shunt with a desired size is formed.

The electrode portion of the expansion body is connected to a conductive wire disposed along a shaft portion and can receive energy supply from an energy application device disposed on a hand side. Such a medical device is disclosed in, for example, International Patent Application Publication No. WO 2019-085841 A.

In a medical device, in a case where an electrode portion is a bipolar electrode or a multipolar electrode portion, if conductive wires connected to the electrode portion are short-circuited at a shaft portion, a risk of heat generation or electric leakage in an unintended portion occurs, and in addition, there is a case where it is not possible to acquire intended potential data. In particular, in a case where a contact portion between the electrode portion and the conductive wire is disposed in the shaft portion, when the shaft portion is bent by receiving an external force at the time of assembly or use of the medical device, there is a possibility that the contact portions of different poles that are electrically independent are short-circuited.

SUMMARY

A medical device that can help prevent short-circuit of a contact portion between an electrode portion and a conductive wire with another contact portion that is electrically independent.

A medical device according to the present disclosure includes an expansion body that is configured to expand and contract in a radial direction, an elongated shaft portion that includes a proximal end fixing portion, to which a proximal end of the expansion body is fixed, at a distal end part, a plurality of electrode assemblies that includes a plurality of electrode portions disposed along the expansion body, and a conductive wire portion disposed in the shaft portion and connected to the electrode assembly with a contact portion, in which at least two or more of the plurality of electrode assemblies are electrically independent, and two or more of the contact portions respectively connected to the two or more electrode assemblies that are electrically independent are disposed at different positions in an axial direction in the shaft portion.

In the medical device configured in this way, when the shaft portion receives the external force and is bent at the time of assembling or using the medical device, the contact portions electrically independent from each other are separated in an axial direction. Therefore, the short-circuit caused by having contact with each other can be prevented.

A voltage may be applied between an electrode pair including the electrode portions included in at least two of the two or more electrode assemblies that are electrically independent from each other. As a result, in a case where the electrode portion is configured as the bipolar electrode, the electrode portions configuring the electrode pair are prevented from being short-circuited at the contact portion.

A plurality of the electrode pairs is disposed, and all the contact portions connected to the electrode assembly may be disposed at positions different from each other in the axial direction in the shaft portion. As a result, in a case where the plurality of the electrode pairs is disposed, all the electrode portions can be prevented from being short-circuited with another electrode portion.

The electrode assembly may include the electrode portion that is disposed along the expansion body and of which a surface has conductivity, an insulation unit that is disposed on a proximal side of the electrode portion and of which a surface is insulated, and the contact portion disposed on a proximal side of the insulation unit. As a result, since a region of the electrode assembly disposed in the shaft portion is not short-circuited in a portion other than the contact portion, by making the axial direction positions of the contact portions be different from each other, it is possible to reliably prevent short-circuit between the electrode portions.

The shaft portion may include an inner layer having a lumen and an outer layer disposed outside the inner layer in a radial direction, and the contact portion may be disposed between the inner layer and the outer layer. As a result, it is possible to reliably prevent leakage of a current.

The shaft portion may include a bending portion that is bent in one direction toward the proximal side, starting from the position of the proximal end fixing portion or on proximal side of the proximal end fixing portion, and the contact portion may be disposed on a proximal side of the bending portion. As a result, the axial direction of the expansion body can be disposed to be close to perpendicular to the surface of the atrial septum with the bending portion, and it is possible to help prevent the contact portion from being damaged by deformation of the bending portion.

An expansion body configured to expand and contract in a radial direction according to the present disclosure includes: a plurality of electrode assemblies that includes plurality of electrode portions disposed along the expansion body; and a conductive wire portion that is disposed in the shaft portion and is connected to the electrode assembly with a contact portion, wherein at least two or more of the plurality of electrode assemblies are electrically independent, and two or more of the contact portions respectively connected to the two or more electrode assemblies that are electrically independent are disposed at different positions in an axial direction in the shaft portion.

A method according the present disclosure for forming a shunt that forms, in an oval fossa, a shunt through which a right atrium communicates with a left atrium using a medical device including an expansion body configured to expand and contract in a radial direction, an elongated shaft portion that includes a proximal end fixing portion, and wherein a proximal end of the expansion body is fixed to the proximal end fixing portion at a distal end part of the elongated shaft, a plurality of electrode assemblies that includes plurality of electrode portions disposed along the expansion body, and a conductive wire portion that is disposed in the shaft portion and is connected to the electrode assembly with a contact portion, wherein at least two or more of the plurality of electrode assemblies are electrically independent, and two or more of the contact portions respectively connected to the two or more electrode assemblies that are electrically independent are disposed at different positions in an axial direction in the shaft portion, the method comprising: inserting the medical device from an inferior vena cava into the right atrium; inserting the expansion body in a contracted state into a hole formed in the oval fossa; expanding the expansion body in the hole to dispose the biological tissue surrounding the hole in the reception space defined by the recess; and cauterizing the biological tissue disposed in the reception space using the plurality of electrode assemblies in contact with the biological tissue.

BRIEF DESCRIPTION OF THE DRAWINGS

FIGS. 11A and 11B are diagrams illustrating a state in S2 in FIG. 10, in which FIG. 11A is an enlarged view of the vicinity of a balloon in the atrial septum illustrated in cross section, and FIG. 11B is a cross-sectional view of the atrial septum for describing a shape of a puncture hole.

FIGS. 12A and 12B are diagrams illustrating a state in S3 in FIG. 10, in which FIG. 12A is an enlarged view of the vicinity of the expansion body illustrating the atrial septum in cross section and the inside of a storage sheath in a transparent manner, and FIG. 12B is a cross-sectional view of the atrial septum in a state in which the storage sheath is inserted through the puncture hole.

DETAILED DESCRIPTION

Figure 1:
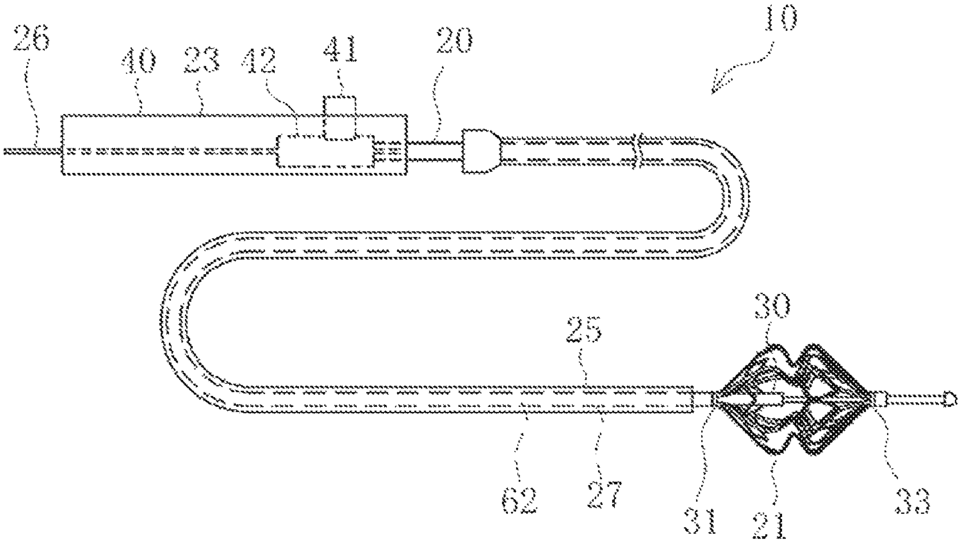
FIG. 1 is a front view illustrating an overall configuration of a medical device according to an embodiment.

Set forth below with reference to the accompanying drawings is a detailed description of embodiments of a medical device that applies energy to a biological tissue. Note that dimensional ratios in the drawings may be exaggerated and different from actual ratios for convenience of description. In addition, here, a side of a medical device 10 to be inserted into a biological lumen will be referred to as a "distal end" or "distal", and an operating hand-side will be referred to as a "proximal end" or "proximal".

The medical device according to the embodiment described below is configured to expand a puncture hole Hh formed in an atrial septum HA of a heart H of a patient, and to further perform a maintenance treatment to maintain the expanded puncture hole Hh at the increased size.

As illustrated in FIG. 1, the medical device 10 according to the present embodiment includes an elongated shaft portion 20, an expansion body 21 disposed at a distal end part of the shaft portion 20, and a hand operation unit 23 disposed at a proximal end part of the shaft portion 20. The expansion body 21 has an electrode portion 22 which is an energy transfer element for performing the above-described maintenance treatment.

The shaft portion 20 has a distal end shaft part 30 including a proximal end fixing portion 31 to which a proximal end of the expansion body 21 is fixed and a distal end fixing portion 33 to which a distal end of the expansion body 21 is fixed. The distal end shaft part 30 extends from the proximal end part of the expansion body 21 to the distal end part, through inside of the expansion body 21.

The shaft portion 20 has a storage sheath 25 disposed at an outermost peripheral portion. The expansion body 21 is movable forward and rearward in an axial direction relative to the storage sheath 25. The storage sheath 25 can house the expansion body 21 therein in a state of moving to the distal side of the shaft portion 20. The expansion body 21 can be exposed by moving the storage sheath 25 from a state of housing the expansion body 21 to the proximal side.

A pulling shaft 26 is disposed in the shaft portion 20. The pulling shaft 26 is disposed from the proximal side of the hand operation unit 23 to the distal side of the expansion body 21, protrudes from the distal end part of the shaft portion 20 to be connected to the distal end part of the expansion body 21, and is slidable with respect to the shaft portion 20. A distal end part of the pulling shaft 26 is fixed to a distal end member 35.

The distal end member 35 to which the distal end part of the pulling shaft 26 is fixed does not need to be fixed to the expansion body 21. As a result, the pulling shaft 26 slides in a proximal end direction with respect to the shaft portion 20 so that the distal end member 35 can apply a compressive force to the expansion body 21 along a shaft center of the shaft portion 20. In addition, when the expansion body 21 is stored in the storage sheath 25, the distal end member 35 is separated to the distal side (i.e. away) from the expansion body 21, by which the expansion body 21 can be rather easily moved in an extending direction. Thus, ease of storage can be improved.

The hand operation unit 23 has a housing 40 gripped by an operator, an operation dial 41 that configured to be rotated by the operator, and a conversion mechanism 42 that operates in conjunction with the rotation of the operation dial 41. The pulling shaft 26 is held by the conversion mechanism 42 inside the hand operation unit 23. The conversion mechanism 42 can move the pulling shaft 26 held by the conversion mechanism 42 forward and backward along the axial direction in conjunction with the rotation of the operation dial 41. A rack and pinion mechanism can be used as the conversion mechanism 42, for example.

It is preferable that the shaft portion 20 be formed of a material having a certain degree of flexibility. Examples of such a material of the shaft portion 20 can include polyolefin such as polyethylene, polypropylene, polybutene, ethylene-propylene copolymer, ethylene-vinyl acetate copolymer, ionomer, or a mixture of two or more of the materials listed above, soft polyvinyl chloride resin, polyamide, polyamide elastomer, polyester, polyester elastomer, polyurethane, fluorine resin such as polytetrafluoroethylene, polyimide, PEEK, silicone rubber, and latex rubber.

The pulling shaft 26 can be formed of, for example, an elongated wire material including a super elasticity alloy such as a nickel-titanium alloy and a copper-zinc alloy, a metal material such as stainless steel, a resin material having comparatively high rigidity, or the like.

The distal end member 35 can be formed of, for example, a super elasticity alloy such as a nickel-titanium alloy or a copper-zinc alloy, a metal material such as stainless steel, a polymer material such as polyolefin, polyvinyl chloride, polyamide, polyamide elastomer, polyurethane, polyurethane elastomer, polyimide, and fluororesin or a mixture of the above polymer materials. Alternatively, the distal end member 35 can be formed of a multilayer tube containing two or more kinds of polymer materials.

Figure 2:
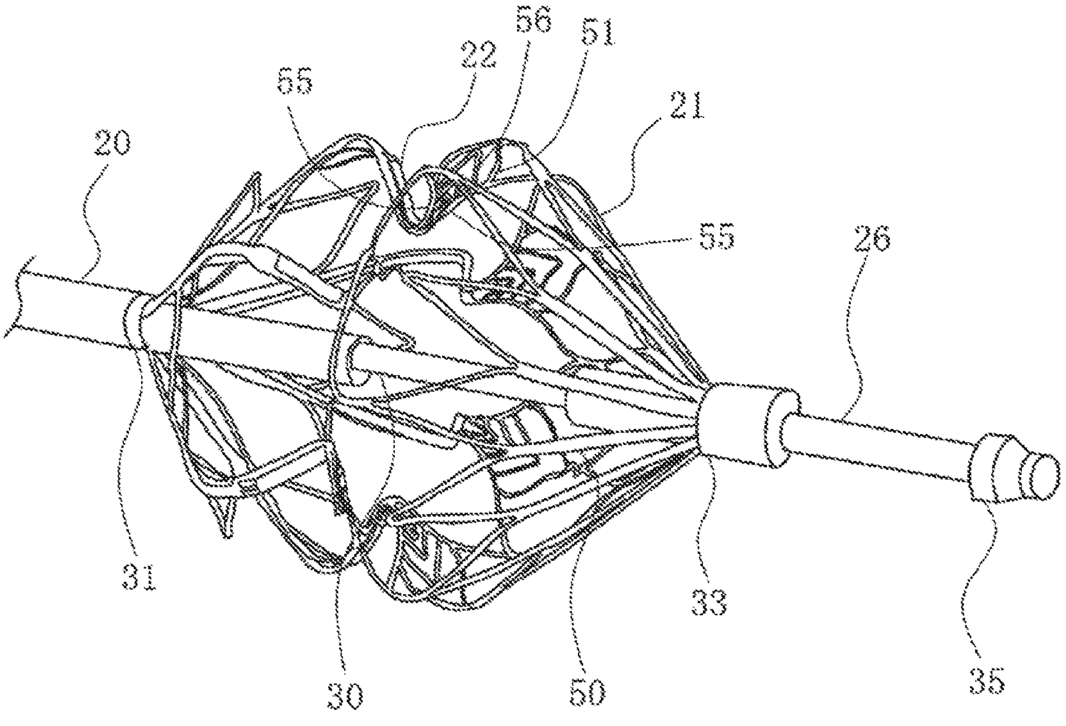
FIG. 2 is an enlarged perspective view of the vicinity of an expansion body.
Figure 3:
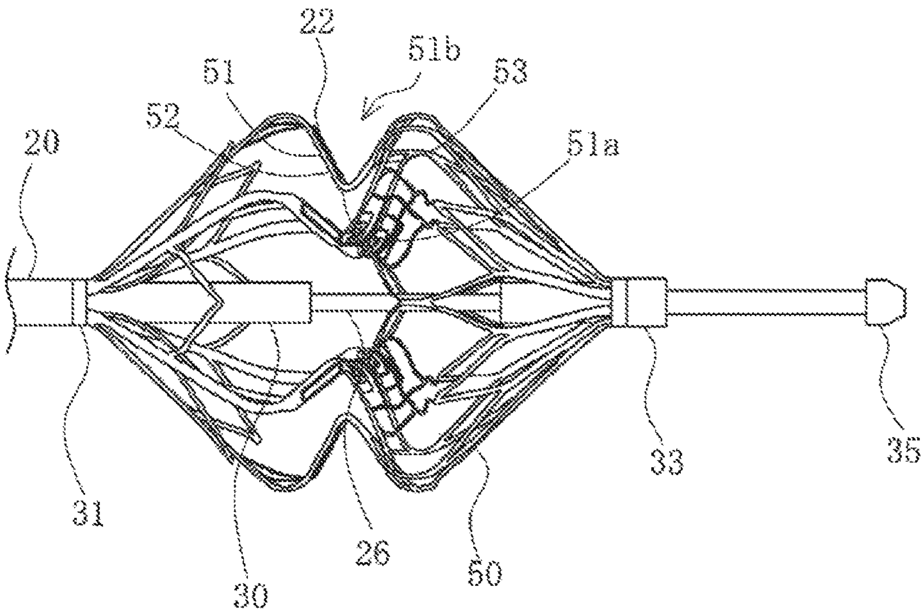
FIG. 3 is an enlarged front view of the vicinity of the expansion body.

Details of the expansion body 21 will be described. As illustrated in FIGS. 2 and 3, the expansion body 21 has a plurality of wire portions 50 in a circumferential direction. The wire portions 50 form a mesh-like structure by branching and joining along a length direction. As a result, the expansion body 21 can expand and contract in a radial direction. A proximal end part of the wire portion 50 extends to the distal side from the proximal end fixing portion 31. A distal end part of the wire portion 50 extends to the proximal side from a proximal end part of the distal end fixing portion 33. The wire portion 50 is inclined to be larger in the radial direction from both ends toward a central part in the axial direction. In addition, the wire portion 50 has a recess 51 in the central part in the axial direction, the recess 51 being recessed radially inward of the expansion body 21. An innermost part of the recess 51 in the radial direction is a bottom portion 51*a*. The recess 51 defines a reception space 51*b* configured to receive a biological tissue when the expansion body 21 expands.

The recess 51 includes a proximal-side upright portion 52 extending radially outward from a proximal end of the bottom portion 51*a* and a distal-side upright portion 53 extending radially outward from a distal end of the bottom portion 51*a*. When the pulling shaft 26 slides in the proximal end direction with respect to the shaft portion 20 and the compressive force is applied to the expansion body 21, the distal-side upright portion 53 and the proximal-side upright portion 52 approach each other, and both have close contact with the biological tissue received in the reception space 51*b*. The electrode portion 22 is disposed along the recess 51 to face the reception space 51*b*, in the proximal-side upright portion 52. In the present embodiment, six electrode portions 22 are disposed along the circumferential direction. The distal-side upright portion 53 includes an outer peripheral portion 55 bifurcated from the vicinity of the bottom portion 51*a* and extending radially outward, and a back support portion 56 disposed between the two outer peripheral portions 55. The electrode portion 22 may be disposed in the distal-side upright portion 53.

The wire portion 50 forming the expansion body 21 can be formed by cutting a single metal cylindrical member with a laser or the like. The wire portion 50 can be formed of a metal material. Examples of the metal material which can be used for the wire portion 50 can include a titanium-based (Ti—Ni, Ti—Pd, Ti—Nb—Sn, or the like) alloy, a copper-based alloy, stainless steel, p-titanium steel, and a Co—Cr alloy. An alloy having a spring property such as a nickel titanium alloy may be more preferably used for the wire portion 50. However, the material of the wire portion 50 is not limited to the above materials, and the wire portion 50 may be formed of other materials.

The electrode portion 22 is connected to an energy supply device that is an external device with a conductive wire portion 66 coated with an insulating coating material. A high-frequency voltage is applied from the energy supply device to an electrode pair including the two electrode portions 22 via the conductive wire portion 66, and energy is applied between these. That is, the electrode portion 22 is configured as a bipolar electrode.

Figure 4A:
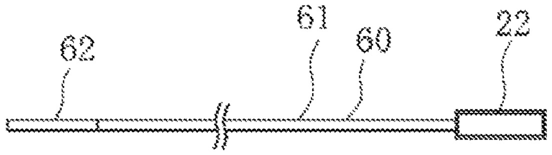
FIGS. 4A and 4B are front view (FIG. 4A) and a cross-sectional view (FIG. 4B) of an electrode assembly.
Figure 4B:
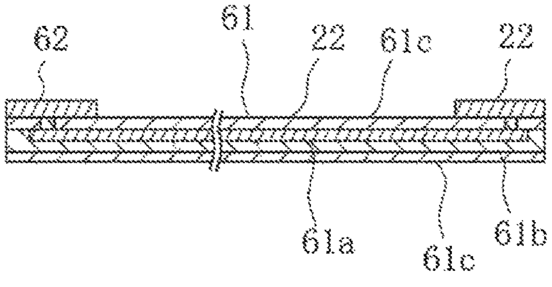

An electrode assembly 60 separated from the expansion body 21 is attached to the expansion body 21. As illustrated in FIG. 4A, the electrode assembly 60 includes an elongated wiring portion 61, the electrode portion 22 disposed at a distal end part of the wiring portion 61, and a contact portion 62 disposed at a proximal end part of the wiring portion 61. As illustrated in FIG. 4B, the wiring portion 61 includes an electric wire portion 61*a* having conductivity. The electric wire portion 61*a*, the electrode portion 22, and the contact portion 62 are formed of metal materials. The electric wire portion 61*a* is embedded in an adhesive layer 61*b* sandwiched between insulation layers 61*c* disposed on surfaces on both sides of the wiring portion 61 in a thickness direction. The electrode portion 22 is disposed to be exposed on a surface of the insulation layer 61*c* and is electrically connected to the electric wire portion 61*a*. Furthermore, the contact portion 62 is a portion that is electrically connecting the electrode assembly 60 to the conductive wire portion 66 disposed on a proximal side of the medical device 10 and is exposed on the surface of the insulation layer 61*c* and is electrically connected to the electric wire portion 61*a*, similarly to the electrode portion 22.

Figure 5:
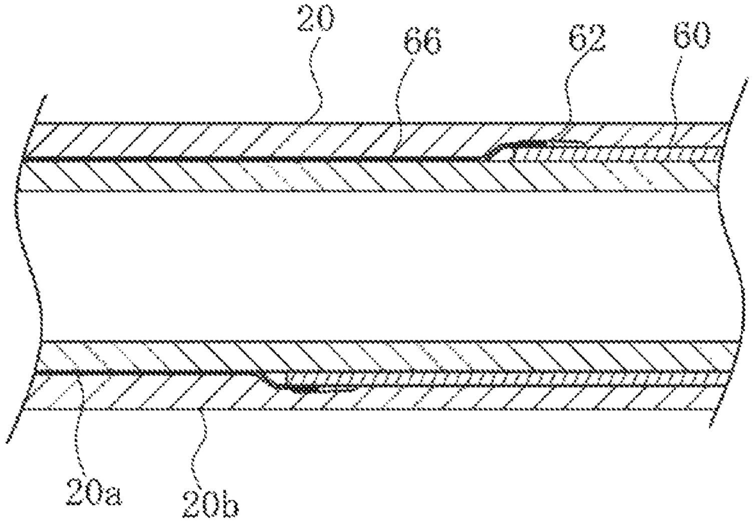
FIG. 5 is a cross-sectional view of a shaft portion and is a diagram of the vicinity of a contact portion.

As illustrated in FIG. 5, the shaft portion 20 includes an inner layer 20*a* having a lumen and an outer layer 20*b* that is disposed outside of the inner layer 20*a* in the radial direction. The electrode assembly 60 and the conductive wire portion 66 are disposed between the inner layer 20*a* and the outer layer 20*b* in the shaft portion 20 and extend along the axial direction. The conductive wire portion 66 is electrically connected to the electrode assembly 60 at the contact portion 62. The two electrode assemblies 60 illustrated in FIG. 5 are electrically independent from each other and are respectively connected to the different conductive wire portions 66. In this case, the contact portions 62 are disposed at different positions in the axial direction in the shaft portion 20.

Figure 6:
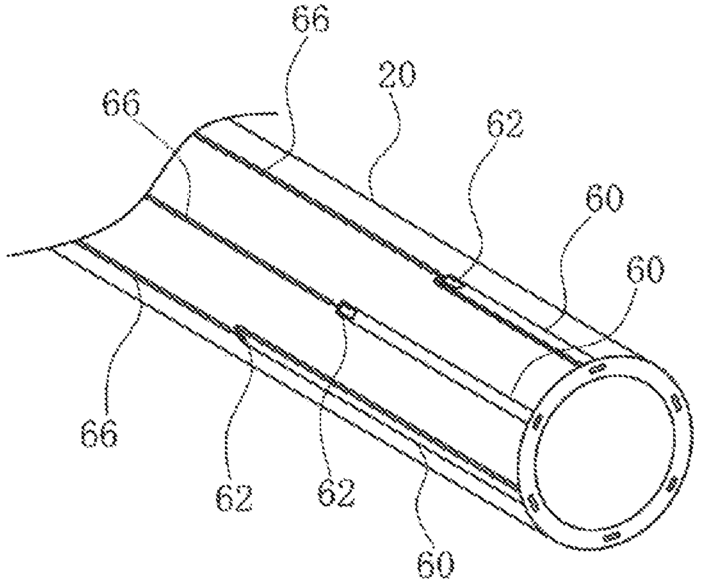
FIG. 6 is a transparent perspective view of the vicinity of the contact portion of the shaft portion.

As illustrated in FIG. 6, the six electrode assemblies 60 are disposed in correspondence with the six electrode portions 22 and along the circumferential direction in the shaft portion 20. All of the contact portions 62 in which the respective electrode assemblies 60 and the conductive wire portions 66 are connected are disposed at different positions in the axial direction in the shaft portion 20.

Figure 7:
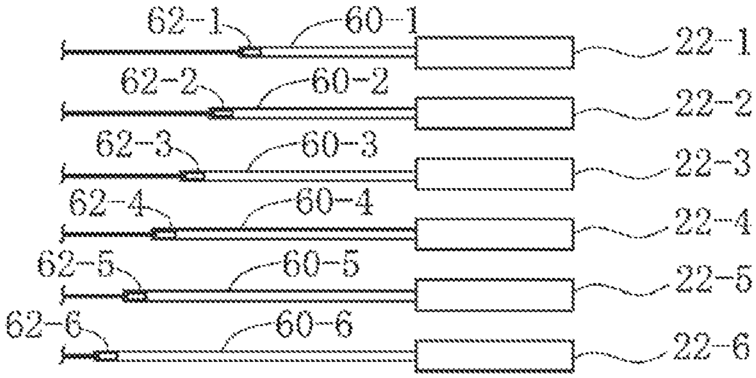
FIG. 7 is a diagram schematically illustrating a wiring relationship between the plurality of electrode assemblies and conductive wires.

In a wiring diagram illustrated in FIG. 7, it is assumed that a voltage is applied between the electrode pair including the adjacent electrode portions 22. For example, an electrode portion 22-1 and an electrode portion 22-2 form an electrode pair. In the example in FIG. 7, contact portions 62-1 to 62-6 of all electrode assemblies 60-1 to 60-6 are disposed at positions different from each other in the axial direction of the shaft portion 20. As a result, when the shaft portion 20 is bent by receiving an external force at the time of assembling or using the medical device 10, it is possible to prevent the contact portions 62 from having contact with each other and short-circuiting.

Figure 8:
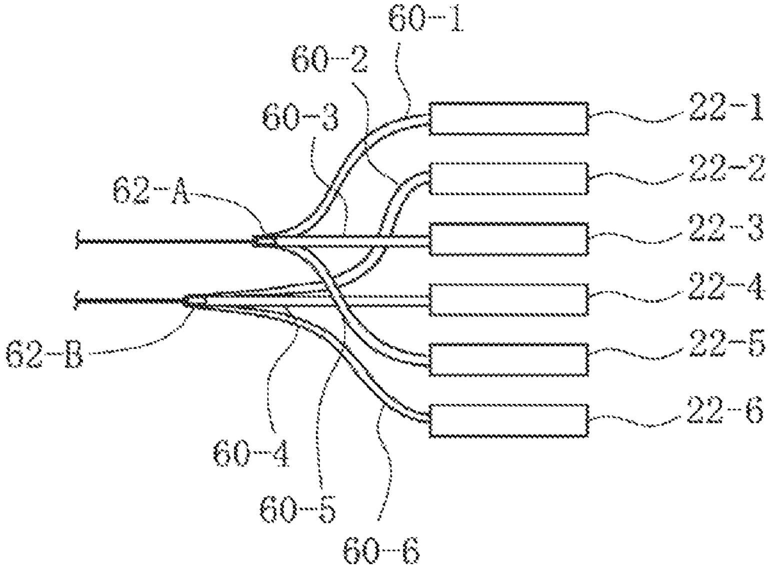
FIG. 8 is a diagram schematically illustrating a wiring relationship according to a modification between the plurality of electrode assemblies and the conductive wires.

Furthermore, as illustrated in FIG. 8, positive electrode portions 22-1, 22-3, and 22-5 may be connected to a single contact portion 62-A, and negative electrode portions 22-2, 22-4, and 22-6 may be connected to a single contact portion 62-B. In this case, the contact portion 62-A and the contact portion 62-B are disposed at positions different from each other in the axial direction of the shaft portion 20.

Figure 9:
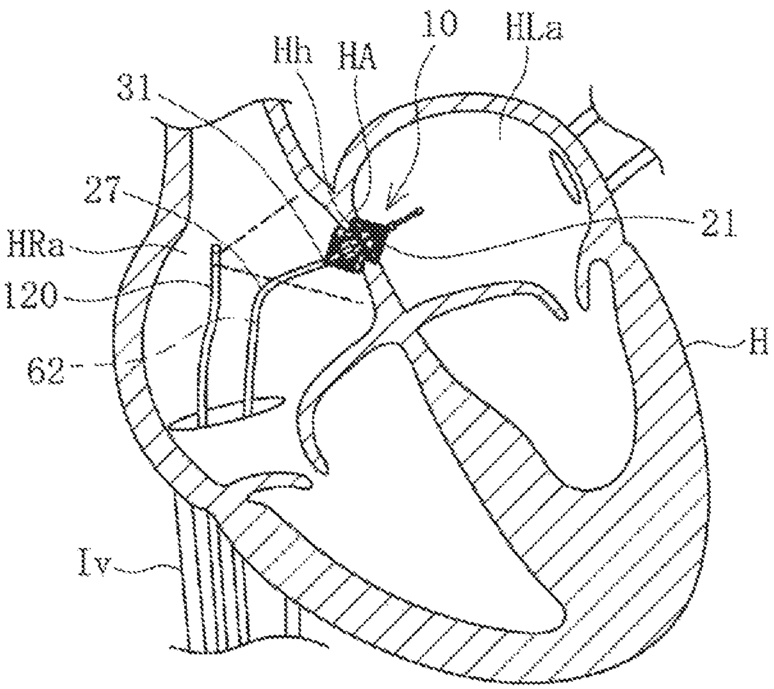
FIG. 9 is an explanatory diagram for schematically illustrating a state in which the expansion body is placed in an atrial septum, including a front view of the medical device and a cross-sectional view of a biological tissue.

A treatment method using the medical device 10 will be described. The treatment method according to the present embodiment is performed on a patient suffering from a heart failure (left heart failure). More specifically, the treatment method is performed on a patient with a chronic heart failure having a high blood pressure in a left atrium HLa due to myocardial hypertrophy appearing in a left ventricle of the heart H and increased stiffness (hardness) as illustrated in FIG. 9.

Figure 10:
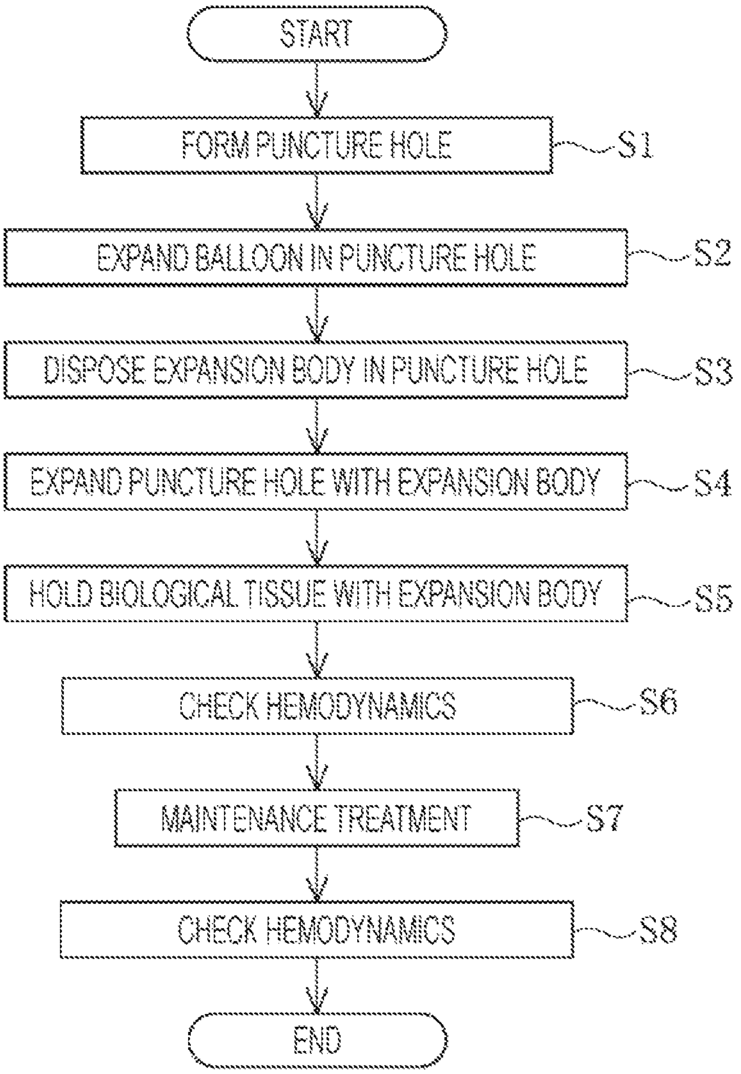
FIG. 10 is a flowchart of a treatment using the medical device.

First, as illustrated in FIG. 10, a puncture hole Hh is formed in the atrial septum HA (S1). In order to form the puncture hole Hh, an operator delivers an introducer obtained by combining a guiding sheath and a dilator to the vicinity of the atrial septum HA. For example, the introducer can be delivered to a right atrium HRa via an inferior vena cava Iv. Furthermore, the introducer can be delivered using a guide wire. The operator can insert the guide wire into the dilator and deliver the introducer along the guide wire. The introducer, the guide wire, or the like can be inserted into a living body with method such as a method for using an introducer to be introduced into a blood vessel.

The operator inserts a puncture device so that the puncture device penetrates from the right atrium HRa side toward the left atrium HLa side, thereby forming the puncture hole Hh. The puncture device is inserted into the dilator and delivered to the atrial septum HA.

Figure 11A:
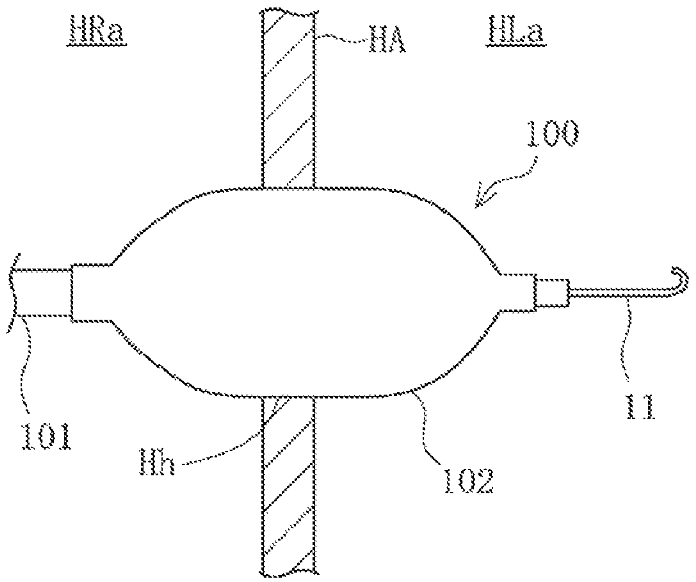
Figure 11B:
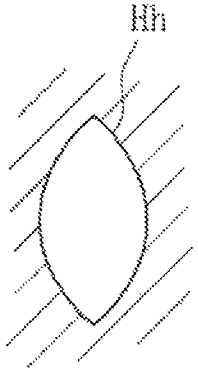

Next, the operator delivers a balloon catheter 100 to the vicinity of the atrial septum HA along the guide wire 11 inserted in advance. The balloon catheter 100 includes a balloon 102 at a distal end part of a shaft portion 101 as illustrated in FIG. 11A. After disposing the balloon 102 in the atrial septum HA, the operator expands the balloon in the radial direction to enlarge the puncture hole Hh (S2) as illustrated in FIG. 11A. At this time, the puncture hole Hh is enlarged to a size equal to the maximum diameter of the expanded balloon 102 in the direction along fibers of the septal tissue due to the influence of the fibers, but is less likely to enlarge in other directions. Therefore, the puncture hole Hh has an elongated shape as illustrated in FIG. 11B.

Next, the medical device 10 is delivered from the inferior vena cava Iv to the vicinity of the atrial septum HA via the right atrium HRa, and the expansion body 21 is disposed at the position of the puncture hole Hh (S3). Although the guide wire is not used for the delivery of the medical device 10, the guide wire may be used for a stable operation with the heart beating.

Figure 12A:
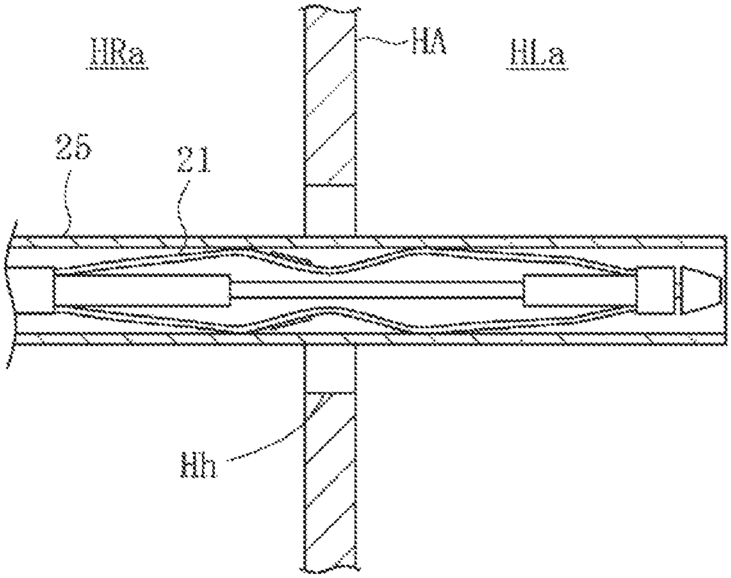
Figure 12B:
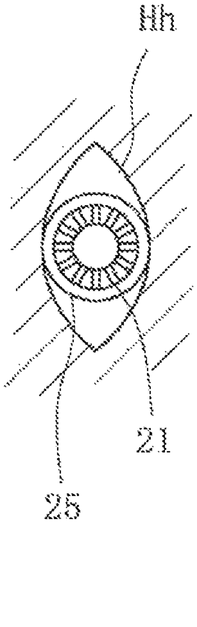

The distal end part of the medical device 10 penetrates the atrial septum HA and reaches the left atrium HLa. In addition, when the medical device 10 is inserted, the expansion body 21 is in a state of being housed in the storage sheath 25 as illustrated in FIG. 12A. Note that, in FIG. 12A and FIGS. 13 and 15, a shape of the expansion body 21 is simplified. Since the puncture hole Hh is enlarged by the balloon 102, the storage sheath 25 can be inserted into the puncture hole Hh as illustrated in FIG. 12B.

Figure 13:
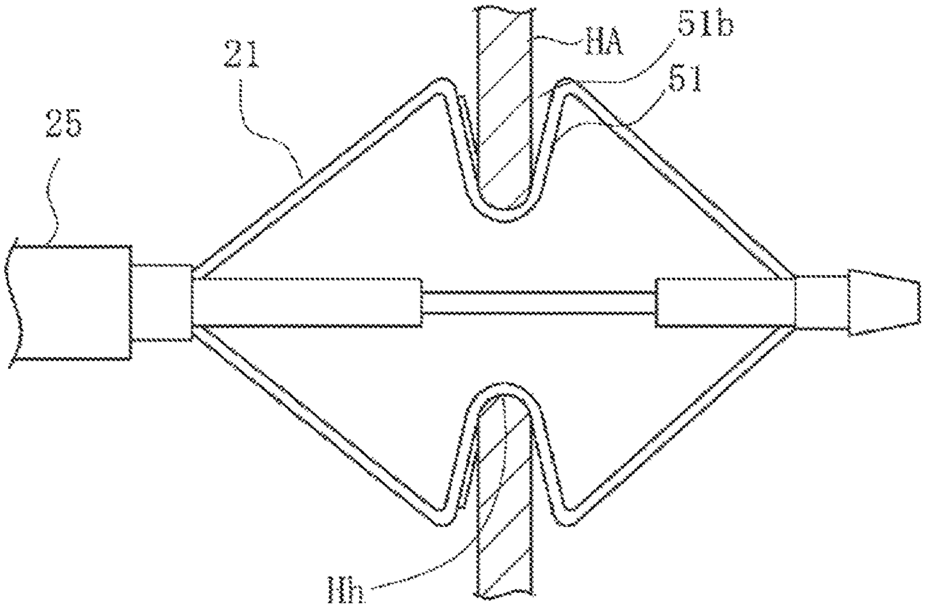
FIG. 13 is a diagram illustrating a state in S4 in FIG. 10, and is an enlarged view of the vicinity of the expansion body in the atrial septum illustrated in cross section.

Next, by moving the storage sheath 25 to the proximal side, the expansion body 21 is exposed, as illustrated in FIG. 13. As a result, the expansion body 21 increases in diameter, and the recess 51 is disposed in the puncture hole Hh of the atrial septum HA and receives the biological tissue surrounding the puncture hole Hh in the reception space 51*b* (S4). As illustrated in FIG. 9, the shaft portion 20 includes a bending portion 27 that is bent toward the proximal side in one direction, starting from a position on the proximal side of the proximal end fixing portion 31. As illustrated in FIG. 1, the bending portion 27 has a linear-shape in a state of being housed in the storage sheath 25 and can be bent in one direction by being exposed from the storage sheath 25. The bending portion 27 may be bent in one direction starting from the proximal end fixing portion 31. The contact portion 62 is disposed on the proximal side of the bending portion 27. As a result, the axial direction of the expansion body 21 can be disposed to be close to perpendicular to the surface of the atrial septum with the bending portion 27, and it is possible to prevent the contact portion 62 from being damaged by deformation of the bending portion 27.

Figure 14:
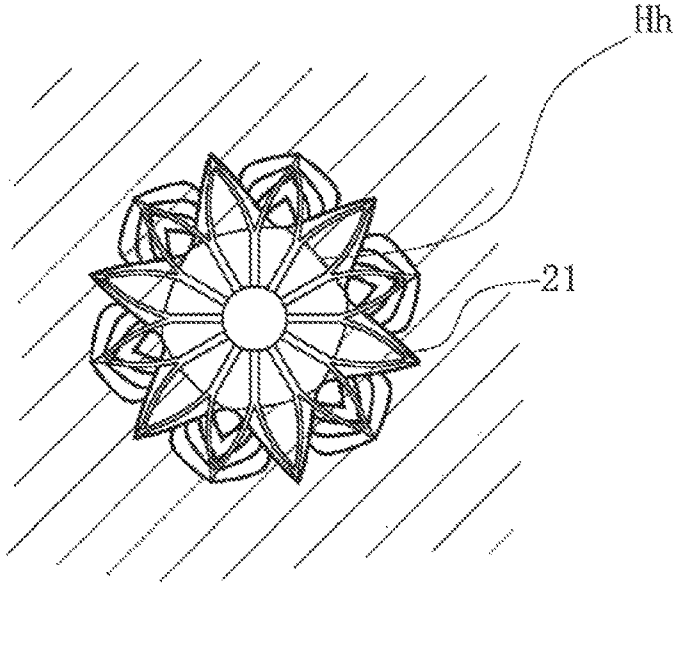
FIG. 14 is a diagram illustrating a state in S4 in FIG. 10, and is a cross-sectional view of the atrial septum in a state in which the puncture hole is enlarged with the expansion body.

Due to the expansion of the expansion body 21, the puncture hole Hh is expanded to have a substantially uniform diameter along the circumferential direction as illustrated in FIG. 14. Although the expansion body 21 changes the shape of the puncture hole Hh, the maximum diameter is not increased. Therefore, the maximum diameter of the puncture hole Hh is equal to the diameter of the puncture hole Hh expanded by the balloon 102 in S2 in the major axis direction.

Figure 15:
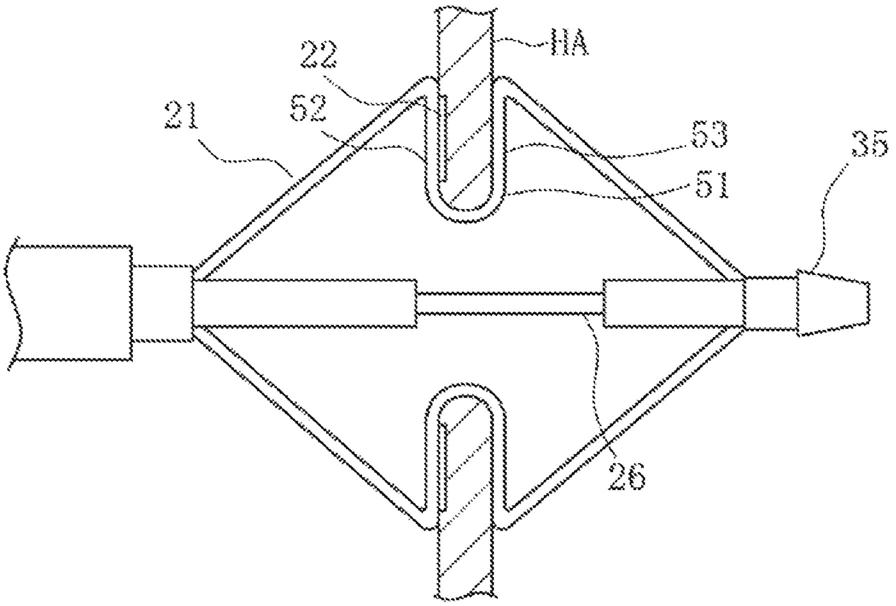
FIG. 15 is a diagram illustrating a state in S5 in FIG. 10, and is an enlarged view of the vicinity of the expansion body in the atrial septum illustrated in cross section.

The operator operates the hand operation unit 23 with the biological tissue being received in the reception space 51*b*, and moves the pulling shaft 26 to the proximal side. With this operation, the expansion body 21 is compressed in the axial direction by being pulled in the compression direction by the distal end member 35, so that the atrial septum HA is held by the proximal-side upright portion 52 and the distal-side upright portion 53, and the electrode portion 22 is pressed against the biological tissue (S5) as illustrated in FIG. 15.

After expanding the puncture hole Hh, the operator checks hemodynamics (S6). The operator delivers a hemodynamics checking device 120 to the right atrium HRa via the inferior vena cava Iv as illustrated in FIG. 9. As the hemodynamics checking device 120, an echo catheter can be used, for example. The operator can display an echo image acquired by the hemodynamics checking device 120 on a display device such as a display, and can check an amount of blood passing through the puncture hole Hh on the basis of the displayed result.

Next, the operator performs the maintenance treatment for inhibiting blockage of the puncture hole Hh due natural healing and maintaining its size (S7). During the maintenance treatment, high-frequency energy is applied to an edge of the puncture hole Hh through the electrode portion 22 to cauterize (heat and cauterize) the edge of the puncture hole Hh by the high-frequency energy. The high-frequency energy is imparted by applying a voltage between the pair of electrode portions 22 adjacent to each other in the circumferential direction.

In a case where the external force is added to the shaft portion 20 until the medical device 10 is inserted into the living body and expanded by the puncture hole Hh and the electrode portion 22 applies the energy to the biological tissue, the contact portions 62 between the electrode assemblies 60 and the conductive wire portions 66 are disposed at the positions different from each other in the axial direction in the shaft portion 20, and accordingly short-circuit of each electrode portion 22 can be prevented. As a result, the energy can be reliably applied to the biological tissue.

When the biological tissue in the vicinity of the edge of the puncture hole Hh is cauterized through the electrode portion 22, a degenerated portion in which the biological tissue is degenerated is formed in the vicinity of the edge. The biological tissue in the degenerated portion loses elasticity, and thus, the puncture hole Hh can maintain the shape enlarged by the expansion body 21.

After performing the maintenance treatment, the operator checks the hemodynamics again (S8). When the amount of blood passing through the puncture hole Hh reaches a desired amount, the operator contracts the expansion body 21, stores the expansion body 21 into the storage sheath 25, and then, removes the expansion body 21 from the puncture hole Hh. Furthermore, the operator removes the entire medical device 10 from the living body to the outside, and ends the treatment.

As described above, the medical device 10 according to the present embodiment includes the expansion body 21 that is configured to expand and contract in the radial direction, the elongated shaft portion 20 having the proximal end fixing portion 31, to which the proximal end of the expansion body 21 is fixed, at the distal end part, the plurality of electrode assemblies 60 including the plurality of electrode portions 22 disposed along the expansion body 21, and the conductive wire portion 66 that is disposed in the shaft portion 20 and is connected to the electrode assembly 60 with the contact portion 62, in which at least two or more of the plurality of electrode assemblies 60 are electrically independent, and two or more of the contact portions 62 respectively connected to the two or more electrode assemblies 60 that are electrically independent are disposed at the different positions in the axial direction in the shaft portion 20. In the medical device 10 configured in this way, when the shaft portion 20 receives the external force and is bent at the time of assembling or using the medical device 10, the contact portions 62 electrically independent from each other are separated in the axial direction. Therefore, the short-circuit caused by having contact with each other can be prevented.

A voltage may be applied between the electrode pair including the electrode portions 22 included in at least two of the two or more electrode assemblies 60 that are electrically independent from each other. As a result, in a case where the electrode portion 22 is configured as the bipolar electrode, the electrode portions 22 configuring the electrode pair are prevented from being short-circuited at the contact portion 62.

A plurality of the electrode pairs is disposed, and all the contact portions 62 connected to the electrode assembly 60 may be disposed at the positions different from each other in the axial direction in the shaft portion 20. As a result, in a case where the plurality of the electrode pairs is disposed, all the electrode portions 22 can be prevented from being short-circuited with another electrode portion 22.

The electrode assembly 60 may include the electrode portion 22 that is disposed along the expansion body 21 and of which the surface having conductivity, an insulation unit 61*c* that is disposed on the proximal side of the electrode portion 22 and of which a surface is insulated, and the contact portion 62 disposed on a proximal side of the insulation unit 61*c*. As a result, since a region of the electrode assembly 60 disposed in the shaft portion 20 is not short-circuited in a portion other than the contact portion 62, by making the axial direction positions of the contact portions 62 be different from each other, it is possible to reliably prevent short-circuit between the electrode portions 22.

The shaft portion 20 may include the inner layer 20*a* having the lumen and the outer layer 20*b* disposed outside the inner layer 20*a* in the radial direction, and the contact portion 62 may be disposed between the inner layer 20*a* and the outer layer 20*b*. As a result, it is possible to reliably prevent leakage of a current.

The shaft portion 20 may include the bending portion 27 that is bent in one direction toward the proximal side, starting from the position of the proximal end fixing portion 31 or on the proximal side of the proximal end fixing portion 31, and the contact portion 62 may be disposed on the proximal side of the bending portion 27. The axial direction of the expansion body 21 can be disposed to be close to perpendicular to the surface of the atrial septum with the bending portion 27, and it is possible to prevent the contact portion 62 from being damaged by the deformation of the bending portion 27.

Note that the present disclosure is not limited to the above-described embodiment, and various modifications can be made by those skilled in the art within the technical idea of the present invention. In the above embodiment, the electrode portion 22 is configured as the bipolar electrode. However, the electrode portion 22 may be two or more monopolar electrodes electrically independent from each other. In this case, electricity is supplied to the electrode portion 22 from a counter electrode plate prepared outside a body.

The detailed description above describes embodiments of a medical device that applies energy to a biological tissue. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:

an expansion body configured to expand and contract in a radial direction;

an elongated shaft portion that includes a proximal end fixing portion, and wherein a proximal end of the expansion body is fixed to the proximal end fixing portion at a distal end portion of the elongated shaft portion;

a plurality of electrode portions disposed along the expansion body;

a conductive wire portion that is disposed in the elongated shaft portion and is connected to the plurality of electrode portions via a contact portion;

wherein the plurality of electrode portions includes a first group of electrode portions having a first polarity and a second group of electrode portions having a second polarity opposite to the first polarity;

the first group of electrode portions is electrically connected to a single first contact portion;

the second group of electrode portions is electrically connected to a single second contact portion; and the single first contact portion and the single second contact portion are disposed at different positions from each other in an axial direction of the elongated shaft portion.

2. The medical device according to claim 1, wherein a voltage is applied between an electrode pair including the electrode portions included in at least two of the two or more electrode assemblies that are electrically independent from each other.

3. The medical device according to claim 2, wherein a plurality of the electrode pairs is disposed, and all the contact portions connected to the electrode assembly are disposed at positions different from each other in the axial direction in the elongated shaft portion.

4. The medical device according to claim 1, wherein the electrode assembly includes the electrode portion that is disposed along the expansion body and of which a surface has conductivity, an insulation unit that is disposed on a proximal side of the electrode portion and of which a surface is insulated, and the contact portion disposed on a proximal side of the insulation unit.

5. The medical device according to claim 1, wherein the elongated shaft portion includes an inner layer having a lumen and an outer layer disposed outside the inner layer in a radial direction, and the contact portion is disposed between the inner layer and the outer layer.

6. The medical device according to claim 1, wherein the elongated shaft portion includes a bending portion that is bent in one direction toward a proximal side, starting from a position of the proximal end fixing portion or on the proximal side of the proximal end fixing portion, and the contact portion is disposed on a proximal side of the bending portion.

7. The medical device according to claim 1, further comprising:

a pulling shaft configured to be disposed in the elongated shaft portion, the pulling shaft is disposed from the proximal side of a hand operation unit to a distal side of the expansion body, protrudes from the distal end portion of the elongated shaft portion to be connected to the distal end portion of the expansion body, and configured to be slidable with respect to the elongated shaft portion.

8. The medical device according to claim 7, wherein a distal end portion of the pulling shaft is fixed to a distal end member, and wherein the distal end member is not fixed to the expansion body.

9. A method for forming a shunt that forms, in an oval fossa, a shunt through which a right atrium communicates with a left atrium using a medical device including an expansion body configured to expand and contract in a radial direction, an elongated shaft portion that includes a proximal end fixing portion, and wherein a proximal end of the expansion body is fixed to the proximal end fixing portion at a distal end portion of the elongated shaft portion, a plurality of electrode portions disposed along the expansion body, and a conductive wire portion that is disposed in the elongated shaft portion and is connected to with the plurality of electrode portions via a contact portion, wherein the plurality of electrode portions includes a first group of electrode portions having a first polarity and a second group of electrode portions having a second polarity opposite to the first polarity, the first group of electrode portions is electrically connected to a single first contact portion, the second group of electrode portions is electrically connected to a single second contact portion, and the single first contact portion and the single second contact portion are disposed at different positions from each other in an axial direction of the elongated shaft portion, the method comprising:

inserting the medical device from an inferior vena cava into the right atrium;

inserting the expansion body in a contracted state into a hole formed in the oval fossa;

expanding the expansion body in the hole to dispose the biological tissue surrounding the hole in the reception space defined by a recess; and cauterizing the biological tissue disposed in the reception space using the plurality of electrode assemblies in contact with the biological tissue.

10. The method according to claim 9, further comprising:

applying a voltage between an electrode pair including the electrode portions included in at least two of the two or more electrode assemblies that are electrically independent from each other.

11. The method according to claim 10, wherein a plurality of the electrode pairs is disposed, and all the contact portions connected to the electrode assembly are disposed at positions different from each other in the axial direction in the elongated shaft portion.

12. The method according to claim 9, wherein the electrode assembly includes the electrode portion that is disposed along the expansion body and of which a surface has conductivity, an insulation unit that is disposed on a proximal side of the electrode portion and of which a surface is insulated, and the contact portion disposed on a proximal side of the insulation unit.

13. The method according to claim 9, wherein the elongated shaft portion includes an inner layer having a lumen and an outer layer disposed outside the inner layer in a radial direction, and the contact portion is disposed between the inner layer and the outer layer.

14. The method according to claim 9, wherein the elongated shaft portion includes a bending portion that is bent in one direction toward a proximal side, starting from a position of the proximal end fixing portion or on the proximal side of the proximal end fixing portion, and the contact portion is disposed on a proximal side of the bending portion.

15. A medical device comprising:

an expansion body configured to expand and contract in a radial direction;

an elongated shaft portion that includes a proximal end fixing portion, and wherein a proximal end of the expansion body is fixed to the proximal end fixing portion at a distal end portion of the elongated shaft;

a plurality of electrode portions disposed along the expansion body;

a conductive wire portion that is disposed in the elongated shaft portion and is connected to the plurality of electrode portions via a contact portion;

wherein the elongated shaft portion includes an inner layer having a lumen and an outer layer disposed outside the inner layer in a radial direction;

wherein the plurality of electrode portions includes a first group of electrode portions having a first polarity and a second group of electrode portions having a second polarity opposite to the first polarity;

wherein the contact portion includes a single first contact portion electrically connected to the first group of electrode portions and a single second contact portion electrically connected to the second group of electrode portions;

wherein each of the single first contact portion and the single second contact portion is disposed between the inner layer and the outer layer; and wherein the single first contact portion and the single second contact portion are physically separated from each other between the inner layer and the outer layer so as to be electrically independent from each other.

16. The medical device according to claim 15, wherein the elongated shaft portion includes a bending portion that is configured to bend in a single predetermined direction relative to a longitudinal axis of a proximal portion of the elongated shaft located proximal to the bending portion, the bending portion being disposed between the proximal end fixing portion of the elongated shaft and the contact portion.

* * * * *